(12) United States Patent
Yamaki et al.

(10) Patent No.: US 11,197,816 B2
(45) Date of Patent: Dec. 14, 2021

(54) COMPOSITION FOR EXTERNAL APPLICATION AND METHOD FOR PRODUCING THE SAME

(71) Applicant: NOF CORPORATION, Tokyo (JP)

(72) Inventors: Hideyuki Yamaki, Chiba (JP); Tomomi Kuromiya, Chiba (JP); Chikako Ichikawa, Chiba (JP); Hisao Ito, Chiba (JP); Mitsuhiro Fukushima, Hyogo (JP); Yuki Munekata, Hyogo (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 16/324,340

(22) PCT Filed: Aug. 8, 2017

(86) PCT No.: PCT/EP2017/070104
§ 371 (c)(1),
(2) Date: Feb. 8, 2019

(87) PCT Pub. No.: WO2018/029209
PCT Pub. Date: Feb. 15, 2018

(65) Prior Publication Data
US 2020/0188285 A1   Jun. 18, 2020

(30) Foreign Application Priority Data

Aug. 9, 2016 (JP) .............................. JP2016-156160

(51) Int. Cl.
*A61K 8/891* (2006.01)
*A61K 8/92* (2006.01)
*A61Q 17/04* (2006.01)
*A61Q 1/02* (2006.01)

(52) U.S. Cl.
CPC .............. *A61K 8/891* (2013.01); *A61K 8/922* (2013.01); *A61Q 1/02* (2013.01); *A61Q 17/04* (2013.01)

(58) Field of Classification Search
None
See application file for complete search history.

(56) References Cited

U.S. PATENT DOCUMENTS

| 7,713,520 | B2 | 5/2010 | Sakuta |
| 8,440,624 | B2 | 5/2013 | Honing et al. |
| 2007/0196291 | A1 | 8/2007 | Sakuta |
| 2011/0261436 | A1 | 10/2011 | Mazurek et al. |

FOREIGN PATENT DOCUMENTS

| CN | 1938000 A | 3/2007 |
| EP | 1736138 A1 | 12/2006 |
| JP | 4745962 B2 | 8/2011 |
| KR | 10-2006-0135026 A | 12/2006 |
| WO | 2009/010356 A1 | 1/2009 |
| WO | 2016/085707 A1 | 6/2016 |

OTHER PUBLICATIONS

International Search Report and Written Opinion, dated Oct. 10, 2017, from corresponding PCT application No. PCT/EP2017/070104.
Office Action issued in Chinese Patent Application No. 201780049408.X dated Jul. 5, 2021.
Office Action issued in Korean Patent Application No. 10-2019-7006845 dated Apr. 21, 2021 with English translation provided.

*Primary Examiner* — Jennifer A Berrios
(74) *Attorney, Agent, or Firm* — Nixon & Vanderhye

(57) ABSTRACT

To provide an acrylic silicone graft copolymer capable of effectively exerting a function in a composition for external application containing various oily components such as a natural oil, a hydrocarbon oil, ester oil and a silicone oil, and a composition for external application containing the acrylic silicone graft copolymer. A composition for external application including an acrylic silicone graft copolymer, which contains 2 to 25 mass % of a constitutional unit represented by formula (I), 55 to 85 mass % of a constitutional unit represented by formula (II) and 2 to 20 mass % of a constitutional unit represented by formula (III). wherein R1 is an alkyl group having 1 to 4 carbon atoms; R2 is an alkylene group having 2 to 10 carbon atoms; and n is an integer of 1 to 100.

12 Claims, No Drawings

COMPOSITION FOR EXTERNAL APPLICATION AND METHOD FOR PRODUCING THE SAME

BACKGROUND OF THE INVENTION

1. Field of the Invention

The present invention relates to a composition for external application containing an acrylic silicone graft copolymer having a predetermined structure and a method for producing the same.

2. Description of Related Art

As a component to be blended in, e.g., skin cosmetics and hair cosmetics, an acrylic silicone graft copolymer containing a constitutional unit represented by a formula (1) and a constitutional unit represented by a formula (2):

[Formula 1]

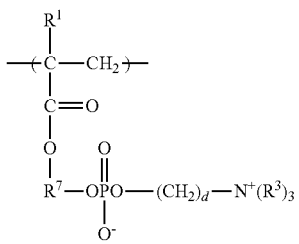

(1)

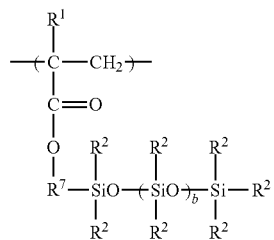

(2)

wherein $R^1$ is hydrogen or methyl; $R^2$ is a fluorine-substituted or unsubstituted alkyl or aryl having 1 to 30 carbon atoms; $R^3$ is alkyl having 1 to 20 carbon atoms; $R^7$ is an aliphatic group; b is an integer of 1 to 300; and d is an integer of 1 to 10 is known (Patent Literature 1).

It is known that since the copolymer is excellent in adhesion to the skin and hair, the copolymer, when blended in skin cosmetics and hair cosmetics, improves spreading of the cosmetics over the skin and prevents comes-off of makeup, and further exerts other functions such as making hair glow and combing hair smooth.

Although the copolymer can effectively exert the function in a composition containing a silicone oil and water, however, the copolymer loses compatibility in the composition and sometimes failed to exert the function when an oily component such as ester oil is blended.

CITATION LIST

Patent Literature

[Patent Literature 1] Japanese Patent No. 4745962

SUMMARY OF CLAIMED SUBJECT MATTER

In these circumstances, it has been desired to provide an acrylic silicone graft copolymer capable of effectively exerting the function in a composition for external application containing various types of oily components such as a hydrocarbon oil, an ester oil and a silicone oil, and a composition for external application containing the acrylic silicone graft copolymer.

Solution to Problem

The present inventors conducted intensive studies with a view to solving the aforementioned problem. As a result, they found that an acrylic silicone graft copolymer having acryl as a main chain, to which a silicone group, a phosphorylcholine group and a benzyl group serving as a side chain are grafted in a predetermined proportion, has good compatibility with not only a silicone oil but also an oily component such as a natural oil, a hydrocarbon oil and an ester oil, and can effectively exert a function in a composition for external application containing various type of oily components. Based on the finding, the present invention was accomplished.

More specifically, the present invention relates to a composition for external application shown below and a method for producing the same, as well as a cosmetic method and the like for skin care or makeup.

[1] A composition for external application comprising an acrylic silicone graft copolymer, which contains 2 to 25 mass % of a constitutional unit represented by formula (I), 55 to 85 mass % of a constitutional unit represented by formula (II) and 2 to 20 mass % of a constitutional unit represented by formula (III):

[Formula 2]

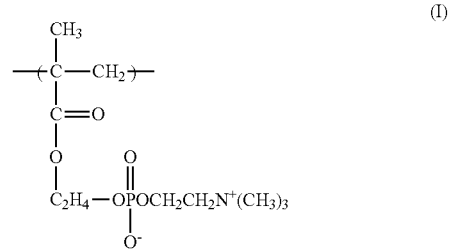

(I)

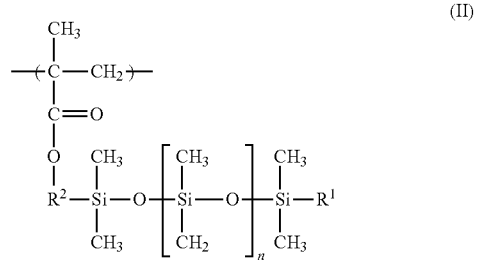

(II)

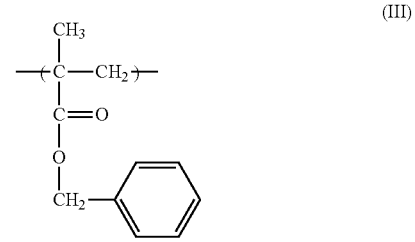

(III)

wherein $R^1$ is an alkyl group having 1 to 4 carbon atoms; $R^2$ is an alkylene group having 2 to 10 carbon atoms; and n is an integer of 1 to 100.

[2] The composition according to [1], further comprising an oily component present in a liquid state at room temperature (25° C.).

[3] The composition according to [2], in which the oily component present in a liquid state at room temperature (25° C.) is at least one selected from the group consisting of a natural oil, a hydrocarbon oil, an ester oil and a silicone oil.

[4] The composition according to any one of [1] to [3], in which the acrylic silicone graft copolymer is contained in an amount of 0.1 to 20 mass % based on the total mass of the composition.

[5] A method for producing the composition according to any one of [1] to [4], comprising blending a mixture of an acrylic silicone graft copolymer and an oily component present in a liquid state at room temperature (25° C.).

[6] Use of the composition according to any one of [1] to [4] for skin care or makeup. [7] A cosmetic method for skin care or makeup, comprising applying the composition according to any one of [1] to [4] to skin.

According to a preferred embodiment of the present invention, it is possible to provide an acrylic silicone graft copolymer that can be stably blended in a composition for external application containing various types of oily components including a natural oil, a hydrocarbon oil, an ester oil, a higher alcohol, a fatty acid and a silicone oil, and provide a composition for external application prepared by blending the acrylic silicone graft copolymer. The acrylic silicone graft copolymer can be blended in a composition for external application for various purposes, for example, as a coating agent, a thickener, a humectant, a conditioning agent and an emulsifying aid. The composition for external application of the present invention can be suitably used as a skin cosmetic (including medicated cosmetic) such as a liquid foundation, a cream foundation, a sunscreen, a makeup base, a face cream, a hand cream and a mascara; a hair cosmetic such as a shampoo, a hair rinse, a hair treatment and a hair cream; and an ointment.

DETAILED DESCRIPTION OF PREFERRED EMBODIMENTS

Now, the composition for external application of the present invention, the method for producing the same, the cosmetic method for skin care or makeup and the like will be described in detail.

The composition for external application of the present invention is characterized by containing an acrylic silicone graft copolymer, which contains 2 to 25 mass % of a constitutional unit represented by formula (I); 55 to 85 mass % of a constitutional unit represented by formula (II); and 2 to 20 mass % of a constitutional unit represented by formula (III):

[Formula 3]

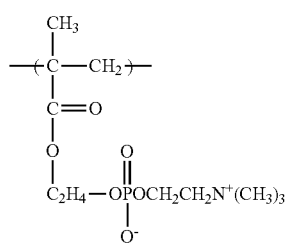
(I)

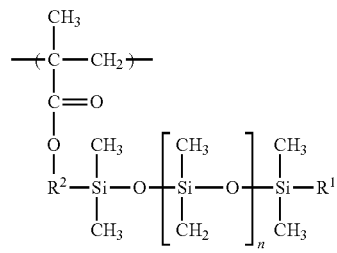
(II)

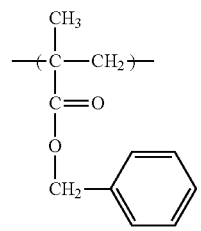
(III)

wherein $R^1$ is an alkyl group having 1 to 4 carbon atoms; $R^2$ is an alkylene group having 2 to 10 carbon atoms; and n is integer of 1 to 100.

In the composition for external application of the present invention, the acrylic silicone graft copolymer can be blended for various purposes, for example, as a coating agent, a thickener, a humectant, a conditioning agent and a moisturizing gent. Since the acrylic silicone graft copolymer can be stably blended in a composition for external application containing various oily components including a natural oil, a hydrocarbon oil, an ester oil, a higher alcohol, a fatty acid and a silicone oil, the acrylic silicone graft copolymer effectively exerts the function in various-form compositions for external application such as an oily composition for external application and various types of emulsions. Now, the composition for external application of the present invention will be more specifically described.

The acrylic silicone graft copolymer to be used in the composition for external application of the present invention contains 2 to 25 mass % of a constitutional unit represented by formula (I), 55 to 85 mass % of a constitutional unit represented by formula (II) and 2 to 20 mass % of a constitutional unit represented by formula (III):

[Formula 4]

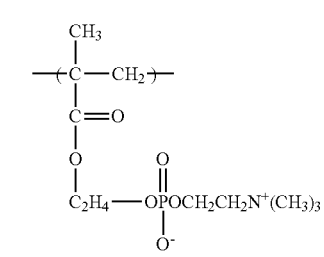
(I)

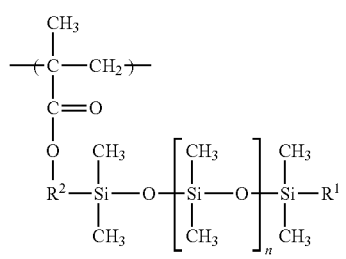

(II)

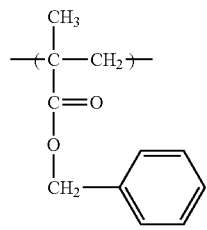

(III)

wherein R¹ is an alkyl group having 1 to 4 carbon atoms; R² is an alkylene group having 2 to 10 carbon atoms; and n is an integer of 1 to 100.

Since the acrylic silicone graft copolymer contains a constitutional unit represented by formula (I), a constitutional unit represented by formula (II) and a constitutional unit represented by formula (III) in the aforementioned ratios, the acrylic silicone graft copolymer has good compatibility with not only a silicone oil but also various oily components such as a hydrocarbon oil and an ester oil and can effectively exert a function in various-form compositions for external application.

In the acrylic silicone graft copolymer to be used in the present invention, the constitutional unit represented by formula (I) accounts for 2 to 25 mass %, preferably 3 mass % or more, more preferably 5 mass % or more and further preferably 7 mass % or more; and preferably 23 mass % or less, more preferably 20 mass % or less and further preferably 17 mass % or less. In the case where the proportion of a constitutional unit represented by formula (I) falls within the above range, the acrylic silicone graft copolymer is stable in a composition containing a silicone oil and water and in the case where the acrylic silicone graft copolymer is used in the composition for external application, adhesion of the composition to skin and hair is satisfactory.

The constitutional unit represented by formula (II) accounts for 55 to 85 mass %, preferably 58 mass % or more, more preferably 60 mass % or more and further preferably 62 mass % or more; and preferably 84 mass % or less, more preferably 83 mass % or less and further preferably 82 mass % or less. In the case where the proportion of the constitutional unit represented by formula (II) falls within the above range, the acrylic silicone graft copolymer has good compatibility with a hydrocarbon oil and a silicone oil and in the case where the acrylic silicone graft copolymer is used in the composition for external application, the persistence of a cosmetic effect is satisfactory.

Note that, in the formula (II), R¹ is an alkyl group having 1 to 4 carbon atoms. Examples of the alkyl group having 1 to 4 carbon atoms include methyl, ethyl, propyl, isopropyl, n-butyl, sec-butyl, isobutyl and tert-butyl.

In the formula (II), R² is an alkylene group having 2 to 10 carbon atoms, preferably an alkylene group having 2 to 8 carbon atoms, and more preferably an alkylene group having carbon 2 to 6 carbon atoms. Preferable examples of the alkylene group having 2 to 10 carbon atoms include ethylene, propylene, isopropylene, n-butylene, isobutylene, sec-butylene, n-pentylene, isopentylene, sec-pentylene, n-hexylene, isohexylene, n-heptylene, isoheptylene, n-octylene, isooctylene, n-nonylene, isononylene, n-decylene and n-isodecylene.

In the formula (II), n is an integer of 1 to 100, preferably 3 or more, more preferably 7 or more and further preferably 10 or more; and an integer of preferably 90 or less, more preferably 70 or less and further preferably 60 or less.

The constitutional unit represented by formula (III) accounts for 2 to 20 mass %, preferably 3 mass % or more, more preferably 5 mass % or more and further preferably 7 mass % or more; and preferably 17 mass % or less, more preferably 15 mass % or less and further preferably 13 mass % or less. In the case where the proportion of the constitutional unit represented by formula (III) falls within the above range, the acrylic silicone graft copolymer has satisfactory compatibility with a hydrocarbon oil, a silicone oil and an ester oil and can be stably blended in a composition containing these oily components.

The acrylic silicone graft copolymer to be used in the present invention may contain other constitutional units besides the aforementioned constitutional units, as long as the object of the invention does not fail to attain. Examples of the other constitutional units include constitutional units obtained from monomers such as acrylic acid, methacrylic acid, an alkyl acrylate, an alkyl methacrylate, a polyoxyalkylene monoacrylate, a polyoxyalkylene monomethacrylate, a glycerin monoacrylate, a glycerin monomethacrylate, a polyglycerin monoacrylate, a polyglycerin monomethacrylate, an acrylamide, a methacrylamide and N-vinyl pyrrolidone.

The acrylic silicone graft copolymer to be used in the present invention can be obtained by addition polymerization of monomers that can provide a constitutional unit represented by formula (I), a constitutional unit represented by formula (II), a constitutional unit represented by formula (III) and an arbitrary constitutional unit, in the presence of a radical polymerization initiator.

As the monomer that can provide a constitutional unit represented by formula (I), compounds represented by formula (Ia) are mentioned.

[Formula 5]

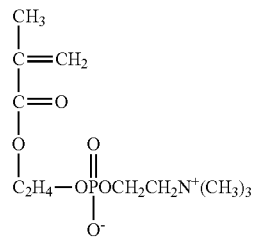

(Ia)

As the monomer that can provide a constitutional unit represented by formula (II), compounds represented by formula (IIa) are mentioned.

[Formula 6]

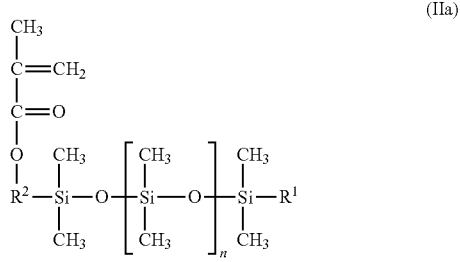

(IIa)

wherein $R^1$ is an alkyl group having 1 to 4 carbon atoms; $R^2$ is an alkylene group having 2 to 10 carbon atoms; n is an integer of 1 to 100.

As the monomer that can provide a constitutional unit represented by formula (III), compounds represented by formula (IIIa) are mentioned.

[Formula 7]

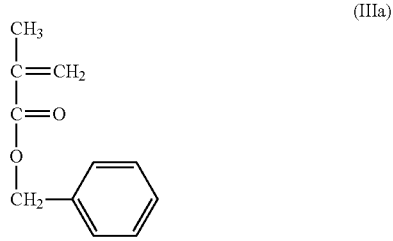

(IIIa)

The starting ratio of individual monomers is preferably the same as the desired ratio of constitutional units.

As a radical polymerization initiator, a radical polymerization initiator having a half-life temperature suitable for polymerization temperature is preferable. Examples thereof include organic peroxides such as dipropyl peroxydicarbonate (T10 (10-hour half-life temperature)=40° C.), benzoyl peroxide (T10=74° C.), lauroyl peroxide (T10=62° C.), t-butyl peroxyhexanoate (T10=72° C.) and t-butyl peroxyneodecanoate (T10=46° C.); and azo compounds such as 2,2'-azobis(2,4-dimethylvaleronitrile) (T10=51° C.) and 2,2'-azobis(isobutyronitrile) (T10=65° C.). These may be used alone or in combination of two or more.

The use amount of a radical polymerization initiator based on the total supply amount of monomers is 0.1 to 20 mass %, more preferably 0.2 mass % or more, further preferably 0.5 mass % or more; and more preferably 10 mass % or less and further preferably 5 mass % or less.

The addition polymerization reaction may be performed, if necessary, in an organic solvent. Examples of the organic solvent include alcohols such as methanol, ethanol, n-propanol, isopropanol, n-butanol, isobutanol, sec-butanol, tert-butanol, n-amyl alcohol, isoamyl alcohol, sec-amyl alcohol, tert-amyl alcohol, 1-ethyl-1-propanol, 2-methyl-1-butanol, n-hexanol and cyclohexanol;

ketones such as methyl ethyl ketone, methyl isobutyl ketone, ethyl butyl ketone, cyclohexanone and isophorone; and ethers such as tetrahydrofuran and dioxane. These organic solvents may be used alone or in combination of two or more. Among them, in view of safety, ethanol is preferable.

The reaction temperature is usually 40 to 120° C. and preferably 50 to 100° C. The reaction time is usually 2 to 24 hours and preferably 5 to 20 hours. After completion of the reaction, volatile components are removed by distillation from a reaction mixture to obtain a desired acrylic silicone graft copolymer.

The content of an acrylic silicone graft copolymer contained in the composition for external application of the present invention is not particularly limited as long as the content is an effective amount and may be appropriately selected depending on, e.g., the purpose, the dosage form and product form. For example, the content of an acrylic silicone graft copolymer based on the total mass of the composition is preferably 0.1 to 20 mass %, more preferably 0.2 mass % or more, further preferably 0.5 mass % or more; and more preferably 15 mass % or less and further preferably 10 mass % or less. In particular, in the case where a makeup lasting effect is desired, the content of an acrylic silicone graft copolymer based on the total mass of the composition is preferably 0.1 to 5 mass % and more preferably 0.5 to 2 mass %. In the case where the function as a thickening agent is expected, the content of an acrylic silicone graft copolymer based on the total mass of the composition is preferably 0.5 to 10 mass % and more preferably 1 to 5 mass %.

The composition for external application of the present invention preferably further contains an oily component present in a liquid state at room temperature (25° C.) in addition to the acrylic silicone graft copolymer. In the case where the acrylic silicone graft copolymer is used as a mixture with an oily component present in a liquid state at room temperature (25° C.), the function of an acrylic silicone graft copolymer can be further effectively exerted in a composition for external application.

The oily component present in a liquid state at room temperature (25° C.) to be used in the present invention is not particularly limited as long as it is usually used in a composition for external application. Among them, e.g., a natural oil, a hydrocarbon oil, an ester oil, a higher alcohol, a fatty acid and a silicone oil is preferable and at least one selected from the group consisting of a hydrocarbon oil, an ester oil, a higher alcohol, a fatty acid and a silicone oil is more preferable. The acrylic silicone graft copolymer to be used in the present invention is highly compatible with not only a silicone oil but also an oily component such as a natural oil, a hydrocarbon oil, an ester oil, a higher alcohol and a fatty acid, and various oily components can be blended in the composition for external application of the present invention.

Examples of the natural oil include avocado oil, Camellia oil, turtle oil, macadamia nut oil, corn oil, mink oil, olive oil, rapeseed oil, egg yolk oil, sesame oil, persic oil, wheat germ oil, Camellia sasanqua oil, castor oil, linseed oil, safflower oil, cotton seed oil, perilla oil, soybean oil, peanut oil, tea seed oil, kaya oil, rice bran oil, Chinese tung oil, Japanese tung oil, jojoba oil, jojoba seed oil, rice germ oil, meadowfoam oil, coconut oil, palm oil, palm kernel oil, fatty acids such as linoleic acid, linolenic acid, caprylic acid, capric acid, isostearic acid, hydrogenated coconut fatty acid and (caprylic/capric acid) coconut alkyl.

Examples of the hydrocarbon oil include alkanes such as paraffin (undecane, tridecane, light paraffin, liquid paraffin), isoparaffin (isodecane, isododecane, isohexadecane, light isoparaffin, hydrogenated polyisobutene), hydrogenated polydecene, squalane, pristane, squalene, cycloparaffin and coconut alkane.

Examples of the ester oil include isononyl isononanoate, isodecyl isononanoate, isotridecyl isononanoate, ethylhexyl isononanoate, neopentyl glycol diisononanate, tricyclodecanemethyl isononanoate, cetyl ethylhexanoate, hexyldecyl ethylhexanoate, neopentyl glycol diethylhexanoate, trimethylolpropane triethylhexanoate, isostearyl palmitate, isopropyl palmitate, trimethylolpropane triethylhexanoate, trimethylolpropane triisostearate, glyceryl tri-2-ethylhexanoate (triethylhexanoin), pentaerythrityl tetraethylhexanoate, isostearyl myristate, isopropyl myristate, isotridecyl myristate, octyldodecyl myristate, isocetyl myristate, dihexyldecylmyristate diethyl sebacate, diethylhexyl sebacate, diisopropyl sebacate, diisopropyl adipate, diisobutyl adipate, dihexyldecyl adipate, isodecyl neopentanoate, hexyl laurate, distearyl malate, isocetyl stearate, butyl stearate, 2-ethylhexyl stearate, hexyldecyl dimethyloctanoate, decyl oleate, octyldodecyl erucate, isobutyl isostearate, isocetyl isostearate, ethyl isostearate, isopropyl isostearate, hexyldecyl isostearate, isostearyl isostearate, caprylic/capric triglyceride, capric triglyceride, diethylhexyl succinate, bisethoxydiglycol succinate, neopentyl glycol diethylhexanate, neopentyl glycol dicaprate and isostearyl neopentanoate.

As the higher alcohol, a higher alcohol having 22 carbon atoms or less is preferable and a higher alcohol having 8 to 18 carbon atoms is more preferable. Examples thereof include isostearyl alcohol, octyldodecanol, oleyl alcohol, decyltetradecanol and hexyldecanol.

As the fatty acid, a fatty acid having 22 carbon atoms or less is preferable and a fatty acid having 6 to 20 carbon atoms is more preferable. Examples thereof include oleic acid, isostearic acid, linoleic acid, linolenic acid, caprylic acid, capric acid, isostearic acid and hydrogenated coconut fatty acid.

Examples of the silicone oil include linear polysiloxanes (for example, dimethicone (dimethylpolysiloxane), methyltrimethic one, caprylylmethicone, phenyltrimethicone, methylphenylpolysiloxane, diphenylpolysiloxane); and cyclicpolysiloxanes (for example, octamethylcyclotetrasiloxane, cyclopentasiloxane, decamethylcyclopentasiloxane, dodecamethylcyclohexasiloxane).

Among them, an oily component having a low viscosity is preferable used in the present invention and an oily component having a rotational viscosity of 100,000 mPa·s or less is more preferable. The rotational viscosity is preferably 10,000 mPa·s or less, more preferably 5,000 mPa·s or less and further preferably 500 mPa·s or less. The "rotational viscosity" herein is defined as the viscosity at 25° C. measured by use of a B type rotational viscometer.

These oily components may be used alone or in combination of two or more.

In the composition for external application of the present invention, the content of the oily component may be appropriately selected depending upon, e.g., the dosage form and product form.

For example, in the case where the composition for external application of the present invention is used as an oily composition for external application, the content of the oily component based on the total mass of the composition is preferably 10 to 99 mass %, more preferably 15 mass % or more and further preferably 20 mass % or more; and more preferably 95 mass % or less and further preferably 90 mass % or less.

In the case where the composition for external application of the present invention is used in a water-in-oil emulsion, the content of an oily component based on the total mass of the composition is preferably 10 to 90 mass %, more preferably 15 mass % or more and further preferably 20 mass % or more; and more preferably 80 mass % or less and further preferably 70 mass % or less.

In the case where the composition for external application of the present invention is used as an oil-in-water emulsion, the content of an oily component based on the total mass of the composition is preferably 10 to 80 mass %, more preferably 15 mass % or more, further preferably 20 mass % or more; and more preferably 70 mass % or less and further preferably 60 mass % or less.

The composition for external application of the present invention may further contain an aqueous component. As the aqueous component, water, a water-soluble solvent or a blend of these is mentioned.

The water-soluble organic solvent is not particularly limited and a water-soluble organic solvent usually used in the composition for external application can preferably be used. Examples thereof include lower alcohols (preferably alcohols having 1 to 5 carbon atoms) such as methanol, ethanol, propanol and isopropanol; and polyhydric alcohols such as ethylene glycol, 1,3-butylene glycol, propylene glycol, dipropylene glycol, isoprene glycol, polyethylene glycol, polyoxyethylene methylglucoside, glycerin and diglycerin. These water-soluble organic solvents may be used alone or in combination of two or more.

In the composition for external application of the present invention, the content of the aqueous component may be appropriately selected depending upon e.g., the dosage form and product form.

For example, in the case where the composition for external application of the present invention is used as an water-in-oil emulsion, the content of the aqueous component based on the total mass of the composition is preferably 5 to 90 mass %, more preferably 10 mass % or more and further preferably 15 mass % or more; and more preferably 80 mass % or less and further preferably 70 mass % or less.

In the case where the composition for external application of the present invention is used as an oil-in-water emulsion, the content of an aqueous component based on the total mass of the composition is preferably 10 to 90 mass %, more preferably 15 mass % or more and further preferably 20 mass % or more; and more preferably 80 mass % or less and further preferably 70 mass % or less.

The composition for external application of the present invention, if desired, can arbitrarily contain a component other than the aforementioned ones as long as the objects and advantages of the present invention does not fail to attain. For example, components that can be blended in compositions for external application such as pharmaceuticals, quasi-drugs or cosmetics can be contained.

Examples of the optional components that can be used in the present invention include a powder component, a surfactant, a solid oil/fat, a wax, a silicone elastomer, a dispersing agent, a co-surfactant, a coating agent, a thickener, a gelatinization agent, an inorganic mineral, a metal sequestering agent, a polyhydric alcohol, a monosaccharide, an oligosaccharide, an amino acid, an organic amine, a polymer emulsion, a vitamin, an antioxidant, an antioxidant aid, a moisturizing agent, a skin softener, an anti-aging agent, anti-staining agent, a keratolytic agent, an antiphlogistine (anti-inflammatory agent), a skin-lightening agent (whitening agents), a skin nutrient, a blood flow accelerator, a disinfectant, a cell (skin) activating agent, a freshener, an astringent, a sunscreen, an antiseptic agent, a plant extract, a buffer and a flagrance, which components can be, if necessary, appropriately added. These optional components may be appropriately selected depending upon e.g., the dosage form and use to be desired.

Examples of the powder component include inorganic powders (for example, talc, kaolin, mica, sericite, muscovite, phlogopite, synthetic mica, deep red mica, biotite, vermiculite, magnesium carbonate, calcium carbonate, aluminum silicate, barium silicate, calcium silicate, magnesium silicate, strontium silicate, tungstic acid metal salt, silica, zeolite, barium sulfate, magnesium sulfate, burnt calcium sulfate (plaster), calcium phosphate, fluorine apatite, hydroxyapatite, ceramic powders, metallic soaps (for example, zinc myristate, calcium palmitate, aluminum stearate, magnesium stearate), boron nitride); organic powders (for example, polyamide resin powder (nylon powder), polyethylene powder, polymethyl methacrylate powder, polystyrene powder, co-polymer resin powder of styrene and acrylic acid, benzoguanamine resin powder, polytetrafluoroethylene powder, cellulose powder); metallic powder pigments (for example, aluminum powder, copper powder), organic pigments such as zirconium, barium or aluminum lakes; and natural pigments (for example, chlorophyll, β-carotene). Here, the powder components may be subjected to a hydrophobic treatment.

The surfactant include an anionic surfactant, a cationic surfactant, an ampholytic surfactant, a lipophilic nonionic surfactant, a hydrophilic nonionic surfactant and a silicone-based surfactant.

Examples of the anionic surfactant include fatty acid soaps (for example, sodium laurate and sodium palmitate); higher alkyl sulfate salts (for example, sodium lauryl sulfate and potassium lauryl sulfate); alkylether sulfate salts (for example, triethanolamine POE-lauryl sulfate and POE-sodium lauryl sulfate); N-acyl sarcosine acids (for example, sodium lauroylsarcosinate); higher fatty acid amide sulfonates (for example, sodium N-myristoyl-N-methyl taurate, sodium cocoyl methyl tauride and sodium lauryl methyltauride); phosphate salts (sodium POE-oleyl ether phosphate, a POE-stearyl ether phosphoric acid, etc.); sulfosuccinates (for example, sodium di-2-ethylhexylsulfosuccinate, sodium monolauroyl monoethanolamide polyoxyethylene sulfosuccinate and sodium lauryl polypropylene glycol sulfosuccinate); alkyl benzenesulfonates (for example, linear sodium dodecylbenzenesulfonate, linear triethanolamine dodecylbenzenesulfonate and a linear dodecylbenzenesulfonic acid); higher fatty acid ester sulfate salts (for example, sodium cocomonoglyceride sulfate); N-acyl glutamates (for example, monosodium N-lauroyl glutamate, disodium N-stearoyl glutamate and monosodium N-myristoyl-L-glutamate); sulfated oils (for example, Turkey red oil); POE-alkylether carboxylic acids; POE-alkylallylether carboxylates; α-olefin sulfonates; higher fatty acid ester sulfonates; secondary alcohol sulfate ester salts; higher fatty acid alkylolamide sulfate ester salts; sodium lauroyl monoethanolamide succinates; ditriethanolamine N-palmitoyl aspartate; and sodium casein.

Examples of the cationic surfactant include alkyltrimethylammonium salts (for example, stearyltrimethylammonium chloride and lauryltrimethylammonium chloride); alkylpyridinium salts (for example, cetylpyridinium chloride); a chloride distearyldimethylammonium dialkyldimethylammonium salt; poly(N,N'-dimethyl-3,5-methylene piperidinium) chloride; alkyl quaternary ammonium salts; alkyldimethylbenzylammonium salts; alkylisoquinolinium salts; dialkylmorpholium salts; POE-alkylamine; alkylamine salts; polyamine fatty acid derivatives; amylalcohol fatty acid derivatives; benzalkonium chloride; and benzethonium chloride.

Examples of the ampholytic surfactant include imidazoline-based ampholytic surfactants (for example, sodium 2-undecyl-N,N,N-(hydroxyethylcarboxymethyl)-2-imidazoline; and a 2-cocoyl-2-imidazolinium hydroxide-1-carboxyethyloxy disodium salt); and betaine-based surfactants (for example, 2-heptadecyl-N-carboxymethyl-N-hydroxyethyl imidazolinium betaine, lauryldimethylamino acetate betaine, alkyl betaine, amide betaine, and sulfobetaine).

Examples of the lipophilic nonionic surfactant include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; glyceryl polyglyceryl fatty acids, such as glyceryl monocottonseed oil fatty acid, glyceryl monoerucate, glyceryl sesquioleate, glyceryl monostearate, glyceryl α,α'-oleate pyroglutamate, and glyceryl monostearate malate; propylene glycol fatty acid esters such as monostearate propylene glycol; a hydrogenated castor oil derivative; a glycerin alkyl ether; and steareth-2.

Examples of the hydrophilic nonionic surfactant include POE-sorbitan fatty acid esters, such as POE-sorbitan monooleate, POE-sorbitan monostearate, POE-sorbitan monooleate and POE-sorbitan tetraoleate; POE sorbitol fatty acid esters, such as POE-sorbitol monolaurate, POE-sorbitol monooleate, POE-sorbitol pentaoleate and POE-sorbitol monostearate; POE-glycerin fatty acid esters, such as POE-glycerin monostearate, POE-glycerin monoisostearate and POE-glycerin triisostearate; POE-fatty acid esters, such as POE-monooleate, POE-distearate, POE-monodioleate and ethylene glycol distearate; POE-alkyl ethers, such as POE-lauryl ether, POE-oleyl ether, POE-stearyl ether, POE-behenyl ether, POE-2-octyldodecyl ether and POE-cholestanol ether; Pluronic type surfactants (e.g., Pluronic); POE-POP-alkyl ethers, such as POE-POP-cetyl ether, POE-POP-2-decyltetradecyl ether, POE-POP-monobutyl ether, POE-POP-hydrogenated lanolin and POE-POP-glycerin ether; and steareth-21.

Examples of a silicone-based surfactant include polyether-modified silicones, such as PEG-10 dimethicone, cetyl PEG/PPG-10/1 dimethicone, PEG-9 polydimethylsiloxyethyl dimethicone, lauryl PEG-9 polydimethylsiloxyethyl dimethicone; polyglycerin-modified silicones, such as polyglyceryl-3 polydimethylsiloxyethyl dimethicone, lauryl polyglyceryl-3 polydimethylsiloxyethyl dimethicone; bis (polyglyceryl-3 oxyphenylpropyl)dimethicone. Further, examples of a silicone-based surfactant include cross-linked polyether-modified silicones (silicone elastomers into which a polyether group has been introduced), such as dimethicone/PEG-10/15 crosspolymer, PEG-15/lauryl dimethicone crosspolymer; cross-linked polyglycerin-modified silicones (silicone elastomers into which a polyglycerin group has been introduced), such as dimethicone/polyglycerin-3, lauryldimethicone/polyglycerin-3 crosspolymer.

Examples of the solid oil/fat (oil/fat which is solid at room temperature (25° C.)) include cacao butter, coconut oil, horse tallow, hardened coconut oil, palm oil, palm kernel oil, Japan tallow kernel oil, hardened oil, Japan tallow, and hardened castor oil.

Examples of the wax include bees wax, candelilla wax, cotton wax, carnauba wax, bayberry wax, Chinese insect wax, montan wax, bran wax, lanolin, kapok wax, acetylated lanolin, liquid lanolin, sugar cane wax, lanolin fatty acid isopropyl ester, hexyl laurate, reduction lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of the silicone elastomer include non-emulsifying organopolysiloxane elastomers and emulsifying organosiloxane elastomers. Examples of the non-emulsifying organopolysiloxane elastomer include dimethicone/vinyl dimethicone crosspolymers and lauryl dimethicone/vinyl dimethicone crosspolymers.

The dimethicone/vinyl dimethicone crosspolymers include products commercially available from DOW CORNING (Midland, Mich.) under the trade names of, for example, "DC 9040" and "DC 9045"; products commercially available from MOMENTIVE under the trade name of "SFE 839" and the "Velvasil" series products; products commercially available from Shin-Etsu Chemical Co., Ltd. under the trade names of, for example, "KSG-15", "KSG-16", and "KSG-18" ([dimethicone/phenyl vinyl dimethicone crosspolymer]); and Gransil™ series products from GRANT INDUSTRIES, Inc.

The lauryl dimethicone/vinyl dimethicone crosspolymers include products commercially available from Shin-Etsu Chemical Co., Ltd. under the trade names of, for example, "KSG-41", "KSG-42", "KSG-43", and "KSG-44".

Further, (lauryl polydimethylsiloxyethyldimethicone/bis-vinyl dimethicone) crosspolymers include products commercially available from Shin-Etsu Chemical Co., Ltd. under the trade names of, for example, "KSG-042Z", "KSG-045Z", and "KSG-048Z".

Examples of the emulsifying organosiloxane elastomer include polyether-modified silicone elastomers, polyalkoxylated silicone elastomers and polyglycerolated silicone elastomers.

The polyether-modified silicone elastomers include (dimethycone(PEG-10/15)) crosspolymers commercially available from Shin-Etsu Chemical Co., Ltd. under the trade names of, for example, "KSG-210" and "KSG-240".

The polyalkoxylated silicone elastomers include products commercially available from DOW CORNING under the trade names of, for example, "DC9010" and "DC9011"; and products commercially available from Shin-Etsu Chemical Co., Ltd. under the trade names of, for example, "KSG-310", "KSG-320", "KSG-330", "KSG-340", "KSG-320Z", "KSG-350Z", "KSG-360Z", and "KSG-380Z".

The polyglycerolated silicone elastomers include products commercially available from Shin-Etsu Chemical Co., Ltd. under the trade names of, for example, "KSG-710", "KSG-810", "KSG-820", "KSG-830" and "KSG-840". In addition, examples of silicone elastomers into which 2 types of branches, i.e., a silicone chain and an alkyl chain have been introduced include products commercially available from Shin-Etsu Chemical Co., Ltd. under the trade names of, for example, "KSG-820Z" and "KSG-850Z".

Silicone elastomers comprising a polyalkyl ether group as pendant or cross-linked may also be used. Particularly suitable silicone elastomers comprising a polyalkyl ether group include compounds with an International Nomenclature of Cosmetic Ingredients (INCH name: bis-vinyldimethicone/bis-isobutyl PPG-20 crosspolymer, bis-vinyldimethicone/PPG-20 crosspolymer, dimethicone/bis-isobutyl PPG-20 crosspolymer, dimethicone/PPG-20 crosspolymer, and dimethicone/bis-secbutyl PPG-20 crosspolymer. Such cross-linked elastomers are available from DOW CORNING under the experimental compound names of, for example, "SOEB-1", "SOEB-2", "SOEB-3" and "SOEB-4", and under the proposed commercial name of, for example, "DC EL-8052 IH Si Organic Elastomer Blend". The elastomer particles are supplied pre-swollen in the respective solvents, isododecane (for SOEB-1 and -2), isohexadecane (for SOEB-3), and isodecyl neopentanoate (for SOEB-4).

As a coating agent, a silicone-based coating agent is preferably mentioned. Examples of the silicone-based coating agent include a silicone resin, an acrylic silicone resin, a silicone-modified pullulan, an adhesive silicone, a fluorosilicone resin and a silicone-urethane coating agent.

Examples of the silicone resin include trimethylsiloxysilicate commercially available from Wacker under the trade name of "Belsil TMS 803"; polypropylsilsesquioxane commercially available from Dow Corning Toray Co., Ltd., under the trade name of "670Fluid"; MQ resin, such as polypropylsilsesquioxane and trimethylsiloxysilicate commercially available under the trade name of "MQ1640 Flake Resin"; and T resin and MTQ resin.

Examples of the acryl silicone resin include an (acrylates/polytrimethylsiloxymethacrylate) copolymer commercially available from Dow Corning Toray Co., Ltd., under the trade name of "FA4002ID Silicone Acrylate" and "FA4001CM Silicone Acrylate"; and an (acrylates/dimethicone) copolymer commercially available from Shin-Etsu Chemical Co., Ltd. under the trade name of "KP-545".

Examples of the silicone-modified pullulan include trimethylsiloxysilylcarbamoyl pullulan commercially available from Shin-Etsu Chemical Co., Ltd. under the trade name of "TSPL-30-ID".

Examples of the adhesive silicone include a trimethylsiloxysilicate/dimethiconol cross-polymer commercially available from Dow Corning Toray Co., Ltd., under the trade name of e.g., "DOW CORNING 7-4411 Cosmetic Fluid".

Examples of the fluorosilicone resin include a trifluoroalkyldimethyltrimethylsiloxysilicate commercially available from Momentive under the trade name of "X566-B8636"; and (trifluoropropyldimethylsiloxy/trimethylsiloxy) silsesquioxane commercially available under the trade name of "FR-5".

Examples of the silicone-urethane coating agent include a bishydroxypropyldimethicone/SMDI copolymer commercially available from Siltech under the trade name of "Silmer UR 5050".

Examples of other coating agents include sucrose acetate isobutyrate commercially available from Eastman Chemical Company under the trade name of "Sustane SAIB"; dextrin isostearate commercially available from Chiba Flour Milling Co., Ltd., under the trade name of "Unifilma HVY"; and a candelilla wax extract commercially available from Ina Trading Co. Ltd. under the trade name of "Candelilla resin E-1".

The water-soluble polymer may be used as the thickener. Examples of the water-soluble polymer include natural polymers such as Arabian gum, carrageenan, karaya gum, tragacanth gum, quince seed (marmelo), casein, dextrin, gelatine, sodium pectate, sodium alginate, locust bean gum, guar gum, tara gum, Tamarind gum, glucomannan, xylan, mannan, xanthan gum, agar, pectin, fucoidan, galactomannan, curdlan, gellan gum, fucogel, casein, collagen, starch, sodium hyaluronate and Alcasealan (*Alcaligenes* Polysaccharides); semi-synthetic polymers such as methylcellulose, ethylcellulose, sodium carboxymethylcellulose, hydroxyethylcellulose, hydroxymethylcellulose, hydroxypropylcellulose, methylhydroxypropylcellulose, hydroxypropylmethylcellulose stearoyl ester, propylene glycol alginate and cellulose dialkyldimethylammonium sulfate; and synthetic polymers such as PVA (polyvinyl alcohol), PVM (polyvinyl methyl ether), PVP (polyvinylpyrrolidone), polyethylene oxide, sodium polyacrylate, carboxyvinyl polymer, acrylate/$C_{10-30}$ alkyl acrylate crosspolymer, and sodium polyacrylate.

Clay minerals may also be used as the thickener. Examples of the clay minerals include one which can provide thickening properties to the water phase such as bentonite, hectorite, magnesium aluminum silicate (veegum) and laponite.

Examples of the metal sequestering agent include 1-hydroxyethane-1,1-diphosphonic acid; tetrasodium 1-hydroxyethane-1,1-diphosphonate salt; disodium edetate; trisodium edetate; tetrasodium edetate; sodium citrate; sodium polyphosphate; sodium metaphosphate; gluconic acid; phosphoric acid; citric acid; ascorbic acid; succinic acid; edetic acid; and trisodium ethylenediaminehydroxyethyl triacetate.

Examples of the polyhydric alcohol include a dihydric alcohol, such as ethylene glycol, propylene glycol, pentylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol and octylene glycol; a trihydric alcohol, such as glycerin and trimethylolpropane; a tetrahydric alcohol such as pentaerythritol (e.g., 1,2,6-hexanetriol); a pentahydric alcohol such as xylitol; a hexahydric alcohol, such as sorbitol and mannitol; a polyhydric alcohol polymer, such as diethylene glycol, dipropylene glycol, triethylene glycol, polypropylene glycol and tetraethylene glycol; dihydric alcohol alkyl ethers, such as ethylene glycol monomethyl ether and ethylene glycol monoethyl ether; dihydric alcohol alkyl ethers, such as diethylene glycol monomethyl ether, diethylene glycol monoethyl ether and diethylene glycol monobutyl ether; a dihydric alcohol ether ester, such as ethylene glycol monomethyl ether acetate and ethylene glycol monoethyl ether acetate; a glycerol monoalkyl ether, such as chimyl alcohol, selachyl alcohol and batyl alcohol; and a sugar alcohol, such as sorbitol, maltitol, maltotriose, mannitol, sucrose, erythritol, glucose, fructose, starch sugar, maltose, xylitose, and a reduced alcohol of a starch sugar.

Examples of the monosaccharide include a triose, such as D-glyceryl aldehyde and dihydroxyacetone; a tetrose, such as D-erythrose, D-erythrulose, D-threose and erythritol; a pentose, such as L-arabinose, D-xylose, L-lyxose, D-arabinose, D-ribose, D-ribulose, D-xylulose and L-xylulose; a hexose, such as D-glucose, D-talose, D-psicose, D-galactose, D-fructose, L-galactose, L-mannose and D-tagatose; a heptose, such as aldoheptose and heprose; an octose such as octurose; a deoxy sugar, such as 2-deoxy-D-ribose, 6-deoxy-L-galactose and 6-deoxy-L-mannose; an amino sugar, such as D-glucosamine, D-galactosamine, sialic acid, amino uronic acid and muramic acid; and an uronic acid, such as D-glucuronic acid, D-mannuronic acid, L-guluronic acid, D-galacturonic acid and L-iduronic acid.

Examples of the oligosaccharide include sucrose, lactose, maltose, trehalose, cellobiose, gentiobiose, umbilicin, raffinose, gentianose, maltotriose, melezitose, planteose, unbelliferose, stachyose, and verbascose.

Examples of the amino acid include a neutral amino acid, such as threonine and cysteine; and a basic amino acid such as hydroxylysine. Further, as an amino acid derivative, for example, sodium acyl sarcosinate (sodium lauroyl sarcosinate), acyl glutamate, sodium acyl β-alanine, glutathione, and pyrrolidone carboxylic acid is exemplified.

Examples of the organic amine include monoethanolamine, diethanolamine, triethanolamine, morpholine, triisopropanolamine, 2-amino-2-methyl-1,3-propanediol, and 2-amino-2-methyl-1-propanol.

Examples of the polymer emulsion include an acrylic resin emulsion, a poly(ethyl acrylate) emulsion, an acrylic resin solution, a poly(alkyl acrylate) emulsion, a poly(vinyl acetate) resin emulsion, and a natural rubber latex.

Examples of the vitamins include vitamins A, $B_1$, $B_2$, $B_6$, C and E and derivatives thereof, pantothenic acid and derivatives thereof and biotin.

Examples of the antioxidants include ascorbic acid and derivatives thereof such as ascorbyl palmitate, ascorbyl tetraisopalmitate, ascorbyl glucoside, magnesium ascorbyl phosphate, sodium ascorbyl phosphate and ascorbyl sorbate; tocopherol and derivatives thereof, such as tocopheryl acetate, tocopheryl sorbate, and other esters of tocopherol; dibutyl hydroxytoluene (BHT) and butylated hydroxyanisole (BHA); gallic acid ester; phosphoric acid; citric acid; maleic acid; malonic acid; succinic acid; fumaric acid; cephalin; a hexametaphosphate; phytic acid; ethylenediaminetetraacetic acid; and plant extracts, for instance from *Chondrus crispus, Rhodiola, Thermus thermophilus*, mate leaves, oak wood, kayu rapet bark, sakura leaves and ylang ylang leaves.

Examples of the moisturizing agent include polyethylene glycol; propylene glycol; dipropylene glycol; glycerin; 1,3-butylene glycol; xylitol; sorbitol; maltitol; mucopolysaccharides such as chondroitin sulfuric acid; hyaluronic acid; sodium hyaluronate; sodium acetyl hyaluronate; mucoitin-sulfuric acid; caronic acid; atelo-collagen; cholesteryl-12-hydroxystearate; a bile salt; a main component of NMF (natural moisturizing factor), such as a pyrrolidone carboxylic acid salt and a lactic acid salt; amino acids such as urea, cysteine and serine; short-chain soluble collagen; a diglycerin (EO) PO addition product; homo- or copolymers of 2-methacryloyloxyethylphosphorylcholine commercially available from NOF Corporation under the names of, for example, Lipidure HM and Lipidure PBM; panthenol; allantoin; PEG/PPG/Polybutylene Glycol-8/5/3 Glycerin commercially available from NOF Corporation under the trade name of "Wilbride S 753"; trimethylglycine commercially available from Asahi Kasei Chemicals Corporation under the trade name of "AMINOCOAT"; and various plant extracts such as *Castanea sativa* extracts, hydrolyzed hazelnut proteins, *Polianthes tuberosa* polysaccharides, *Argania spinosa* kernel oil, and an extract of pearl containing conchiolin commercially available from Maruzen Pharmaceuticals Co., Ltd. under the trade name of "Pearl Extract" ®.

Examples of the skin softener include glyceryl polymethacrylate and methyl gluceth-20.

Examples of the anti-aging agent include acyl amino acids (specifically for example, products commercially available from SEDERMA, S.A.S. under the trade names of "Maxilip", "Matrixyl L 3000" and "Biopeptide CL", and a product commercially available from SEPPIC under the trade name of "Sepilift"); *Pisum sativum* extracts; hydrolyzed soy proteins; methylsilanol mannuronate; hydrolyzed *cucurbita pepo* seedcake; and *Scenedesmus* extracts.

Examples of the anti-staining agents include Moringa pterygosperma seed extracts (specifically, such as a product commercially available from LSN under the trade name of "Purisoft"); and Shea butter extracts (specifically, for example, products commercially available from SILAB under the trade name of "Detoxyl", and a blend of an ivy extract, phytic acid and a sunflower seed extract (for example, a product commercially available from SEDERMA, S.A.S. under the trade name of "OSMOPUR")).

Examples of the keratolytic agents include α-hydroxy acids (specifically, for example, glycolic, lactic, citric, malic, mandelic and tartaric acids), β-hydroxy acids (specifically, for example, salicylic acid), esters thereof (specifically, $C_{12-13}$ alkyl lactate), and plant extracts containing these hydroxy acids (specifically, for example, Hibiscus sabdriffa extracts).

Examples of the anti-inflammatory agents include bisabolol, allantoin, tranexamic acid, zinc oxide, sulfur oxide and derivatives thereof, chondroitin sulfate, and glycyrrhizinic acid and derivatives thereof (for example, glycyrrhizinates).

The composition for external application of the present invention may also contain at least one whitening agent to block the synthesis of structural proteins such as the melanocyte-specific protein Pmel17 involved in the mechanism of melanogenesis (stage I). Examples of such a whitening agent include the ferulic acid-containing cytovector (water, glycol, lecithin, ferulic acid, and hydroxyethylcellulose) commercially available from BASF under the trade name of "Cytovector" ®.

Furthermore, the composition for external application of the present invention may contain at least one peptide as described in WO2009/010356.

Furthermore, the composition for external application of the present invention may include a whitening agent having an inhibitory effect on melanin synthesis, on nanophthalmia-related transcription factor expression, on an anti-tyrosinase activity and/or on endothelin-1 synthesis. Examples of such a whitening agent include a *Glycyrrhiza glabra* extract commercially available from Maruzen Pharmaceuticals Co., Ltd. under the trade name of "Licorice extract" ®.

Furthermore, the composition for external application of the present invention may include whitening agents having an antioxidant action as well, such as vitamin C compounds, which include ascorbate salts, ascorbyl esters of fatty acids or of sorbic acid, and other ascorbic acid derivatives. Specific examples include ascorbyl phosphates (magnesium ascorbyl phosphate, sodium ascorbyl phosphate, and the like), and saccharide esters of ascorbic acid (ascorbyl-2-glucoside, 2-O-α-D-glucopyranosyl L-ascorbate, 6-O-β-D-galactopyranosyl L-ascorbate, and the like). Active agents of this type are commercially available from DKSH under the trade name of "Ascorbyl glucoside" ®.

Furthermore, the composition for external application of the present invention may include other whitening agents. Examples of the other whitening agents include pigmentation inhibiting agents such as plant extracts (e.g., *Narcissus tazetta* extracts), cetyl tranexamate (Nikko Chemicals Co., Ltd; trade name: "NIKKOL TXC"), arbutin, kojic acid, ellagic acid, cysteine, 4-thioresorcin, resorcinol or rucinol or derivatives thereof, glycyrrhizinic acid and hydroquinone-β-glucoside.

Furthermore, the composition for external application of the present invention may also include organic and/or inorganic sunscreens.

Examples of the organic sunscreens include dibenzoylmethane derivatives such as butyl methoxydibenzoylmethane (for example, a product commercially available from HOFFMANN LA ROCHE under the trade name of "Parsol 1789"); cinnamic acid derivatives such as octyl methoxycinnamate (for example, a product commercially available from HOFFMANN LA ROCHE under the trade name of "Parsol MCX"); salicylates; para-aminobenzoic acids; (343'-diphenylacrylate derivatives; benzophenone derivatives; benzylidenecamphor derivatives such as terephtalylidene dicamphor sulphonic acid; phenylbenzimidazole derivatives; triazine derivatives; phenylbenzotriazole derivatives; and anthranilic acid derivatives, all of which may be coated or encapsulated.

Examples of the inorganic sunscreens include pigments and nanopigments formed from coated or uncoated metal oxides. Examples of the nanopigments include titanium oxide, iron oxide, zinc oxide, zirconium oxide and cerium oxide, which are all well-known as UV photoprotective agents.

Examples of the antiseptic agent include p-oxybenzoate ester (e.g., methylparaben and propylparaben) and phenoxyethanol.

In addition, as an optional component to be used in the composition for external application of the present invention, those mentioned in the "International Cosmetic Ingredient Dictionary and Handbook", 13th Edition, 2010, published by the Personal Care Products Council, can be used.

The amounts of these optional components contained are not particularly limited as long as the optional components are in a range which does not impair the object of the present invention.

The dosage form of the composition for external application of the present invention is not particularly limited; however, since the acrylic silicone graft copolymer to be contained in the composition for external application of the present invention can effectively exert the function in an oily component, the external application of the present invention is preferably used in the form of an oily composition for external application or various emulsion forms.

The product form of the composition for external application of the present invention is not particularly limited and can arbitrarily be selected. The composition for external application of the present invention can be used, for example, in facial cosmetics such as facial cleanser, lotion, beauty essence, milky lotion, cream and pack; makeup cosmetics such as foundation, lipstick, eye shadow, sunscreen and makeup bases; body cosmetics; aromatic cosmetics; body cleaning products; hand creams; hair cosmetics such as shampoo, hair rinse, hair treatment and hair cream; and ointments.

The composition for external application of the present invention can be produced by appropriately selecting components depending upon the dosage form and product form, blending and stirring them.

Since the acrylic silicone graft copolymer contained in the composition for external application of the present invention can effectively exert the function in an oily component, it is preferable, in the present invention, that an acrylic silicone graft copolymer is previously blended with an oily component and then added to a composition for external application.

In the composition for external application of the present invention, an acrylic silicone graft copolymer can effectively exert a function as a coating agent, a thickener, a humectant, a conditioning agent and an emulsifier aid.

According to a preferred embodiment of the present invention, for example, in the case where the composition for external application of the present invention is used as a cosmetic composition for skin care or makeup, a cosmetic composition excellent in persistence of a cosmetic effect such as makeup effect and skin care effect, can be obtained even if another coating agent is not blended. Furthermore, in the case where the composition for external application of the present invention is used as a cosmetic composition for skin care or makeup, the cosmetic composition is stable even if another thickener is not blended and a cosmetic composition having a characteristic viscosity can be obtained. Moreover, in the case where the composition for external application of the present invention is used as a cosmetic composition for skin care or makeup, a cosmetic composition, which is a stable and emulsified composition, can be obtained even if the content of a surfactant is reduced. As described above, the present invention provides a cosmetic method for skin care or makeup including applying the composition for external application of the present invention to skin. Note that, in the specification, "cosmetic effect" includes not only a makeup effect but also a skin care effect.

According to a preferred embodiment of the present invention, in the case where the composition for external application of the present invention is used as hair cosmetics, hair glow and smooth combing can be made even if another conditioning agent is not blended.

For example, in the case where the composition for external application of the present invention is used as an ointment, an ointment excellent in efficacy persistence can be obtained even if another coating agent is not blended. For example, in the case where the composition for external application of the present invention is used as an ointment, an ointment stable and having a characteristic viscosity can be obtained even if another thickener is not blended.

Note that, the composition for external application of the present invention, if necessary, may contain another coating agent, thickener, surfactant, humectant, conditioning agent and emulsifier aid.

EXAMPLES

Now, the present invention will be more specifically described by way of Examples and Comparative Examples; however, the present invention is not limited to these Examples. Note that, unless otherwise specified, the composition ratio is based on mass ratio (mass %).

[Copolymer of Synthesis Examples 1 to 3]

Copolymers shown in Table 1 were obtained by the following synthesis.

1. To a glass flask equipped with a stirrer, a thermometer and a reflux condenser, 2-methacryloyloxyethyl phosphorylcholine represented by the formula (I), siloxanyl methacrylate represented by the formula (II), benzyl methacrylate represented by the formula (III), ethanol and tert-butyl peroxyneodecanoate were added individually in accordance with the contents represented by part by mass shown in Table 1. The mixture was heated under a nitrogen stream and polymerized at 50° C. for 12 hours and thereafter at 70° C. for 3 hours.

2. Volatile components were removed by distillation under reduced pressure to obtain an acrylic silicone graft copolymer.

TABLE 1

Raw materials and composition ratios of acrylic silicone graft copolymers of Synthesis Examples 1 to 3

|  |  | Synthesis Example 1 | Synthesis Example 2 | Synthesis Example 3 |
|---|---|---|---|---|
| Raw material (parts by mass) | 2-Methacryloyloxyethyl phosphorylcholine*[1] | 10 | 10 | 10 |
|  | Siloxanyl methacrylate; molecular weight 1000*[2] | 80 | — | — |
|  | Siloxanyl methacrylate; molecular weight 2100*[3] | — | 80 | — |
|  | Siloxanyl methacrylate; molecular weight 4600*[4] | — | — | 80 |
|  | Benzyl methacrylate | 10 | 10 | 10 |
|  | Ethanol | 310 | 310 | 310 |
|  | Tertiary butyl peroxyneodecanoate*[5] | 1.3 | 1.3 | 1.3 |
| Composition ratio (%) | 2-Methacryloyloxyethyl phosphorylcholine | 10 | 10 | 10 |
|  | Siloxanyl methacrylate; molecular weight 1000 | 80 | — | — |
|  | Siloxanyl methacrylate; molecular weight 2100 | — | 80 | — |
|  | Siloxanyl methacrylate; molecular weight 4600 | — | — | 80 |
|  | Benzyl methacrylate | 10 | 10 | 10 |

*[1] manufactured by NOF Corporation
*[2] manufactured by Shin-Etsu Chemical Co., Ltd.
*[3] manufactured by Shin-Etsu Chemical Co., Ltd.
*[4] manufactured by Shin-Etsu Chemical Co., Ltd.
*[5] manufactured by NOF Corporation Comparative Synthesis Examples 1 to 4

The acrylic silicone graft copolymers shown in Table 2 were obtained by the following synthesis.

1. To a glass flask equipped with a stirrer, a thermometer and a reflux condenser, 2-methacryloyloxyethyl phosphorylcholine represented by the formula (I), siloxanyl methacrylate represented by the formula (II), benzyl methacrylate represented by the formula (III), ethanol and tert-butyl peroxyneodecanoate were added individually in accordance with the contents represented by part by mass shown in Table 2. The mixture was heated under a nitrogen stream and polymerized at 50° C. for 12 hours and thereafter at 70° C. for 3 hours.

2. Volatile components were removed by distillation under reduced pressure, an acrylic silicone graft copolymer was obtained.

TABLE 2

Raw materials and composition ratios of Comparative Synthesis Examples 1 to 4

|  |  | Comparative Synthesis Example 1 | Comparative Synthesis Example 2 | Comparative Synthesis Example 3 | Comparative Synthesis Example 4 |
|---|---|---|---|---|---|
| Raw material (part by mass) | 2-Methacryloyloxyethyl phosphorylcholine*[1] | 50 | 10 | 10 | 10 |
|  | Siloxanyl methacrylate; molecular weight 2100*[2] | 50 | 90 | 50 | 60 |
|  | Benzyl methacrylate | — | — | 40 | 30 |
|  | Ethanol | 310 | 310 | 310 | 310 |
|  | Tertiary butyl peroxyneodecanoate*[3] | 1.3 | 1.3 | 1.3 | 1.3 |
| Composition ratio (%) | 2-Methacryloyloxyethyl phosphorylcholine | 50 | 10 | 10 | 10 |
|  | Siloxanyl methacrylate | 50 | 90 | 50 | 60 |
|  | Benzyl methacrylate | — | — | 40 | 30 |

*[1] manufactured by NOF Corporation
*[2] manufactured by Shin-Etsu Chemical Co., Ltd.
*[3] manufactured by NOF Corporation

[Compatibility of Copolymers of Synthesis Examples 1 to 3 and Comparative Synthesis Examples 1 to 4]

Each (1 g) of the copolymers obtained by the aforementioned methods was mixed with individual solvent components (2 g) shown in Table 3 and the appearance thereof was visually observed and shown in Table 3.

TABLE 3

Compatibility of copolymers of Synthesis Examples 1 to 3 and Comparative Synthesis Examples 1 to 3

| Solvent component | Synthesis Example 1 | Synthesis Example 2 | Synthesis Example 3 | Comparative Synthesis Example 1 | Comparative Synthesis Example 2 | Comparative Synthesis Example 3 | Comparative Synthesis Example 4 |
|---|---|---|---|---|---|---|---|
| Isododecane | Transparently swollen | Transparently swollen | Transparently swollen | Not swollen | Not swollen | Swollen | Swollen |
| Methyl trimethicone | Transparently swollen | Transparently swollen | Transparently swollen | Not swollen | Not swollen | Not swollen | Not swollen |
| Dimethylpolysiloxane 2CS | Transparently swollen | Transparently swollen | Transparently swollen | Not swollen | Not swollen | Not swollen | Not swollen |
| Decamethylcyclopentasiloxane | Transparently swollen | Transparently swollen | Transparently swollen | Not swollen | Not swollen | Not swollen | Not swollen |
| Isononyl isononanoate | Transparently swollen | Transparently swollen | Transparently swollen | Not swollen | Not swollen | Not swollen | Not swollen |

An acrylic silicone graft copolymer, in which a benzyl methacrylate was introduced, showed compatibility with C12 hydrocarbon, i.e., isododecane. The acrylic silicone graft copolymer further showed compatibility with a silicone oil such as methyl trimethicone, dimethylpolysiloxane, decamethylcyclopentasiloxane or an ester oil such as isononyl isononanoate by controlling the introduction ratio of benzyl methacrylate.

[Water-in-Oil Foundations of Examples 1 to 3, Comparative Examples 1 and 2]

Compositions for external application, i.e., water-in-oil foundations were prepared in accordance with formulations shown in Table 4, as follows.

1. To each of the copolymers of Synthesis Examples 1 to 3, the same mass of ethanol was added, stirred and mixed until homogeneous to obtain mixtures as components 7 to 9. Then, to the mixtures (components 7 to 9), methyl trimethicone (component 10) was added, stirred and mixed until homogeneous to obtain copolymer mixtures.

2. Components 1 to 6 were mixed until homogeneous to obtain a paste-like mixture.

3. Next, each of the copolymer mixtures and the paste-like mixture were combined and further components 11 to 15 were sequentially added and mixed until homogeneous. In this manner, oil phase mixtures were obtained.

4. Separately, components 16 to 20 were stirred until homogeneous to obtain an aqueous phase mixture.

5. Finally, to the oil phase mixtures, the aqueous phase mixture was added with stirring. In this manner, the compositions for external application, i.e., water-in-oil foundations, of Examples 1 to 3 and Comparative Examples 1 and 2 were individually obtained.

TABLE 4

| Component | Example 1 | Example 2 | Example 3 | Comparative Example 1 | Comparative Example 2 |
|---|---|---|---|---|---|
| | | | | unit: mass % | |
| 1 PEG-9 polydimethylsiloxyethyl dimethicone | 2.50 | 2.50 | 2.50 | 2.50 | 2.50 |
| 2 Methyl trimethicone | 4.00 | 4.00 | 4.00 | 4.00 | 4.00 |
| 3 Caprylyl methicone | 3.50 | 3.50 | 3.50 | 3.50 | 3.50 |
| 4 Hydrophobized titanium oxide particles | 7.00 | 7.00 | 7.00 | 7.00 | 7.00 |
| 5 Hydrophobized titanium oxide pigment | 6.00 | 6.00 | 6.00 | 6.00 | 6.00 |
| 6 Hydrophobized iron oxide | 4.00 | 4.00 | 4.00 | 4.00 | 4.00 |
| 7 Mixture of copolymer of Synthesis Example 1 and ethanol | 3.00 | — | — | — | — |
| 8 Mixture of copolymer of Synthesis Example 2 and ethanol | — | 6.00 | — | — | — |
| 9 Mixture of copolymer of Synthesis Example 3 and ethanol | — | — | 10.00 | — | — |
| 10 Methyl trimethicone | 13.00 | 10.00 | 16.00 | — | — |
| 11 Coating agent: trimethylsiloxysilicate (KF7312T, manufactured by Shin-Etsu Chemical Co., Ltd.) | — | — | — | — | 4.00 |
| 12 Methyl trimethicone | 15.00 | 15.00 | 5.00 | 31.00 | 27.00 |
| 13 Ultraviolet absorber: Ethylhexyl methoxycinnamate | 6.00 | 6.00 | 6.00 | 6.00 | 6.00 |
| 14 Spherical powder: polymethylsilsesquioxane | 2.50 | 2.50 | 2.50 | 2.50 | 2.50 |
| 15 Hydrophobized mica | 1.50 | 1.50 | 1.50 | 1.50 | 1.50 |
| 16 Purified water | 25.00 | 25.00 | 25.00 | 25.00 | 25.00 |
| 17 Glycerin | 3.50 | 3.50 | 3.50 | 3.50 | 3.50 |
| 18 Magnesium sulfate | 0.50 | 0.50 | 0.50 | 0.50 | 0.50 |
| 19 Butylene glycol | 2.00 | 2.00 | 2.00 | 2.00 | 2.00 |
| 20 Preservative: Phenoxyethanol | 1.00 | 1.00 | 1.00 | 1.00 | 1.00 |
| Total | 100.00 | 100.00 | 100.00 | 100.00 | 100.00 |

[Appearance of Water-in-Oil Foundation Prepared]

The compositions for external application prepared were allowed to stand still at 40° C. for 6 months and the presence or absence of separation was visually checked. The results are shown in Table 5.

[Evaluation of Cosmetic-Effect Persistency]

Cosmetic-effect persistency of the liquid foundations prepared was evaluated based on the following evaluation criteria. The results are shown in Table 5.

Evaluation criteria of cosmetic-effect persistency:
10 panelists used the liquid foundation prepared (a nonhomogeneous composition for external application was stirred and mixed immediately before application).

A: 8 or more out of 10 panelists felt that persistency of makeup was satisfactory.

B: 7 out of 10 panelists felt that persistency of makeup was satisfactory.

C: 4 to 6 out of 10 panelists felt that persistency of makeup was satisfactory.

D: 3 out of 10 panelists felt that persistency of makeup was satisfactory.

The water-in-oil foundations of Examples 1 to 3, in which the copolymers of Synthesis Examples 1 to 3 were blended, respectively, were successfully obtained as a homogeneous-state composition for external application and confirmed to have excellent cosmetic-effect persistency.

[Water-in-Oil Foundations of Examples 4 and 5 and Comparative Examples 3 and 4]

Compositions for external application, i.e., water-in-oil foundations were prepared in accordance with the formulations shown in Table 6, as follows.

1. To the copolymer of Synthesis Example 2, the same mass of ethanol was added, stirred and mixed until homogeneous to obtain a mixture as component 7. Then, to the mixture (component 7), hydrogenated coconut fatty acid and coconut alkyl (caprylate/caprate) (component 8 and 9) were added, stirred and mixed until homogeneous to obtain a copolymer mixture.

2. Components 1 to 6 were mixed until homogeneous to obtain a paste-like mixture.

TABLE 5

| | Example 1 | Example 2 | Example 3 | Comparative Example 1 | Comparative Example 2 |
|---|---|---|---|---|---|
| Appearance of cosmetic foundation, standstill at 40° C. for 6 months after preparation | Skin color is homogeneous | | | Clear liquid is separated | |
| Cosmetic-effect persistency | B | A | A | D | C |

3. Next, the copolymer mixture and the paste-like mixture were combined and further components 10 to 16 were sequentially added and mixed until homogeneous to obtain an oil phase mixture.

4. Separately, components 17 to 22 were stirred until homogeneous to obtain an aqueous phase mixture.

5. Finally, to the oil phase mixture, the aqueous phase mixture was added with stirring. In this manner, the compositions for external application, i.e., water-in-oil foundations of Examples 4 and 5 and Comparative Examples 3 and 4 were individually obtained.

TABLE 6 unit: mass %

| | Component | Example 4 | Example 5 | Comparative Example 3 | Comparative Example 4 |
|---|---|---|---|---|---|
| 1 | Polyglyceryl-3 diisostearate | 1.00 | 1.00 | 1.00 | 1.00 |
| 2 | Hydrogenated coconut fatty acid | 4.00 | 4.00 | 4.00 | 4.00 |
| 3 | Coconut alkyl (caprylate/caprate) | 1.00 | 1.00 | 1.00 | 1.00 |
| 4 | Hydrophobized titanium oxide particles | 10.00 | 10.00 | 10.00 | 10.00 |
| 5 | Hydrophobized titanium oxide pigment | 7.00 | 7.00 | 7.00 | 7.00 |
| 6 | Hydrophobized iron oxide | 4.00 | 4.00 | 4.00 | 4.00 |
| 7 | Mixture of copolymer of Synthesis Example 2 and ethanol | 3.00 | 10.00 | — | — |
| 8 | Hydrogenated coconut fatty acid | 10.00 | 10.00 | 10.00 | 10.00 |
| 9 | Coconut alkyl (caprylate/caprate) | 2.00 | 2.00 | 2.00 | 2.00 |
| 10 | Coating agent: dextrin isostearate (UNIFILMA HVY, manufactured by Chiba Flour Milling Co., Ltd.) 50% + coconut alkyl (caprylate/caprate) 50% | — | — | — | 2.00 |
| 11 | Ultraviolet absorber: ethylhexyl methoxycinnamate | 6.00 | 6.00 | 6.00 | 6.00 |
| 12 | Disteardimonium hectorite | 1.00 | — | 2.00 | 2.00 |
| 13 | Hydrogenated coconut fatty acid | 10.00 | 5.00 | 12.00 | 10.00 |
| 14 | Coconut alkyl (caprylate/caprate) | 1.50 | 0.50 | 2.50 | 1.50 |
| 15 | Aluminum starch octenylsuccinate | 3.00 | 3.00 | 3.00 | 3.00 |
| 16 | Hydrophobized cellulose beads | 3.00 | 3.00 | 3.00 | 3.00 |
| 17 | Purified water | 25.00 | 25.00 | 25.00 | 25.00 |
| 18 | Glycerin | 3.00 | 3.00 | 3.00 | 3.00 |
| 19 | Magnesium sulfate | 0.50 | 0.50 | 0.50 | 0.50 |
| 20 | Butylene glycol | 2.00 | 2.00 | 2.00 | 2.00 |
| 21 | Ethanol | 2.00 | 2.00 | 2.00 | 2.00 |
| 22 | Preservative: phenoxyethanol | 1.00 | 1.00 | 1.00 | 1.00 |
| | Total | 100.00 | 100.00 | 100.00 | 100.00 |

It was confirmed that the water-in-oil foundations of Example 4 and 5, in which the copolymer of Synthesis Example 2 was blended, was excellent in cosmetic-effect persistency even if a coating agent was not blended. Furthermore, the water-in-oil foundation of Example 5, in which the copolymer of Synthesis Example 2 was blended in a large amount, was stable even if a thickener was not blended and a foundation having characteristic viscosity was obtained. In contrast, in Comparative Example 3, cosmetic-effect persistency was not sufficient; whereas in Comparative Example 4, since a coating agent and a thickener were added, the user felt sticky when used.

[Water-in-Oil Foundations of Examples 6, 7 and Comparative Example 5]

Compositions for external application, i.e., water-in-oil foundations were prepared in accordance with the formulations shown in Table 7, as follows.

1. To the copolymer of Synthesis Example 2, the same mass of ethanol was added, stirred and mixed until homogeneous to obtain a mixture as component 7. Then, to the mixture (component 7), cyclopentasiloxane (component 8) was added, stirred and mixed until homogeneous to obtain a copolymer mixture.

2. Components 1 to 6 were mixed until homogeneous to obtain a paste-like mixture.

3. Next, the copolymer mixture and the paste-like mixture were combined and further components 9 to 15 were sequentially added and mixed until homogeneous to obtain an oil phase mixture.

4. Separately, components 16 to 21 were stirred until homogeneous to obtain an aqueous phase mixture.

5. Finally, to the oil phase mixture, the aqueous phase mixture was added with stirring. In this manner, the compositions for external application, i.e., water-in-oil foundations of Examples 6 and 7 and Comparative Example 5 were individually obtained.

TABLE 7 unit: mass %

| | Component | Example 6 | Example 7 | Comparative Example 5 |
|---|---|---|---|---|
| 1 | PEG-10 dimethicone | 2.00 | 2.00 | 2.00 |
| 2 | Cyclopentasiloxane | 4.00 | 4.00 | 4.00 |
| 3 | Hydrophobized talc | 2.00 | 2.00 | 2.00 |
| 4 | Hydrophobized titanium oxide particles | 8.00 | 8.00 | 8.00 |
| 5 | Hydrophobized titanium oxide pigment | 6.00 | 6.00 | 6.00 |
| 6 | Hydrophobized iron oxide | 4.00 | 4.00 | 4.00 |
| 7 | Mixture of copolymer of Synthesis Example 2 and ethanol | 3.00 | 10.00 | — |
| 8 | Cyclopentasiloxane | 10.00 | 10.00 | 10.00 |
| 9 | (Dimethicone/(peg-10/15)) cross polymer (KSG-210, manufactured by Shin-Etsu Chemical Co., Ltd.) | 5.00 | — | 8.00 |
| 10 | Antioxidant: tocopherol acetate | 0.50 | 0.50 | 0.50 |
| 11 | Ultraviolet absorber: ethylhexyl methoxycinnamate | 6.00 | 6.00 | 6.00 |
| 12 | Isononyl isononanoate | 4.00 | 4.00 | 4.00 |
| 13 | Dimethicone | 4.00 | 4.00 | 4.00 |
| 14 | Caprylyl methicone | 4.00 | 4.00 | 4.00 |
| 15 | Spherical powder: polymethylsilsesquioxane | 4.00 | 4.00 | 4.00 |
| 16 | Purified water | 25.00 | 25.00 | 25.00 |

TABLE 7-continued

| Component | Example 6 | Example 7 | Comparative Example 5 |
|---|---|---|---|
| 17 Glycerin | 3.00 | 3.00 | 3.00 |
| 18 Magnesium sulfate | 0.50 | 0.50 | 0.50 |
| 19 Butylene glycol | 2.00 | 2.00 | 2.00 |
| 20 Ethanol | 2.00 | — | 2.00 |
| 21 Preservative: phenoxyethanol | 1.00 | 1.00 | 1.00 |
| Total | 100.00 | 100.00 | 100.00 | unit: mass %

It was confirmed that the water-in-oil foundations of Examples 6 and 7, in which the copolymer of Synthesis Example 2 was blended, were excellent in cosmetic-effect persistency even if a coating agent was not blended. Furthermore, the water-in-oil foundation of Example 7, in which the copolymer of Synthesis Example 2 was blended in a large amount, was stable even if a thickener was not blended and a foundation having characteristic viscosity was obtained. In contrast, in Comparative Example 5, since a thickener was contained in a large amount for stabilization of the preparation, the user felt sticky when used.

[Nonaqueous Foundations of Examples 8 and 9, Comparative Example 6 and 7]

Compositions for external application, i.e., water-in-oil foundations were prepared in accordance with the formulations shown in Table 8 as follows.

1. To the copolymer of Synthesis Example 2, the same mass of ethanol was added, stirred and mixed until homogeneous to obtain a mixture as component 8. Then, to the mixture (component 8), cyclopentasiloxane (component 9) was added, stirred and mixed until homogeneous to obtain a copolymer mixture.

2. Components 1 to 7 were mixed until homogeneous to obtain a paste-like mixture.

3. Next, the copolymer mixture and the paste-like mixture were combined and further components 10 to 21 were sequentially added and mixed until homogeneous. In this manner, the compositions for external application, i.e., non-aqueous foundations, of Examples 8 and 9, Comparative Examples 6 and 7 were obtained.

TABLE 8

| Component | Example 8 | Example 9 | Comparative Example 6 | Comparative Example 7 |
|---|---|---|---|---|
| 1 Lauryl PEG-9 polydimethylsiloxyethyl dimethicone | 1.00 | 1.00 | 1.00 | 1.00 |
| 2 Phenyltrimethicone | 4.00 | 2.00 | 4.00 | 4.00 |
| 3 Caprylyl methicone | 4.00 | 6.00 | 4.00 | 4.00 |
| 4 Hydrophobized titanium oxide particles | 8.00 | 8.00 | 8.00 | 8.00 |
| 5 Hydrophobized titanium oxide pigment | 6.00 | 6.00 | 6.00 | 6.00 |
| 6 Hydrophobized iron oxide | 4.50 | 4.50 | 4.50 | 4.50 |
| 7 Hydrophobized mica | 2.00 | 2.00 | 2.00 | 2.00 |
| 8 Mixture of copolymer of Synthesis Example 2 and ethanol | 4.00 | 10.00 | — | — |
| 9 Cyclopentasiloxane | 10.00 | 12.00 | 10.00 | 12.00 |
| 10 Disteardimonium hectorite | — | — | 1.00 | 1.00 |
| 11 (Dimethicone/vinyl dimethicone) crosspolymer (KSG-16, manufactured by Shin-Etsu Chemical Co., Ltd.) | 4.00 | — | 5.00 | 5.00 |
| 12 Coating agent: trifluoropropyl dimethyl trimethylsiloxy silicic acid (X566-B8226, manufactured by Momentive) | — | — | 2.00 | — |
| 13 Triethylhexanom | 10.00 | 10.00 | 10.00 | 10.00 |
| 14 Ultraviolet absorber: ethylhexyl methoxycinnamate | 6.00 | 6.00 | 6.00 | 6.00 |
| 15 Polybutene | 10.00 | 9.00 | 10.00 | 10.00 |
| 16 Isododecane | 10.00 | 10.00 | 10.00 | 10.00 |
| 17 Preservative: caprylyl glycol | 0.50 | 0.50 | 0.50 | 0.50 |
| 18 Spherical powder: vinyl dimethicone/methicone silsesquioxane crosspolymer | 4.00 | 4.00 | 4.00 | 4.00 |
| 19 Spherical powder: polymethylsilsesquioxane | 5.00 | 5.00 | 5.00 | 5.00 |
| 20 Ethanol | 6.00 | 3.00 | 6.00 | 6.00 |
| 21 Preservative: phenoxyethanol | 1.00 | 1.00 | 1.00 | 1.00 |
| Total | 100.00 | 100.00 | 100.00 | 100.00 | unit: mass %

It was confirmed that the nonaqueous foundations of Examples 8 and 9, in which the copolymer of Synthesis Example 2 was blended, was excellent in cosmetic-effect persistency even if a coating agent was not blended. Furthermore, the nonaqueous foundation of Example 9, in which the copolymer of Synthesis Example 2 was blended in a large amount, was stable even if a thickener was not blended and a foundation having characteristic viscosity was obtained. In contrast, in Comparative Example 6, since a thickener and a coating agent were blended, the user felt squeakiness when used. In Comparative Example 7, cosmetic-effect persistency was not sufficient.

[Water-in-Oil Sunscreens of Example 10 and Comparative Example 8]

Compositions for external application, i.e., water-in-oil sunscreens were prepared in accordance with the formulations shown in Table 9 as follows.

1. To the copolymer of Synthesis Example 2, the same mass of ethanol was added, stirred and mixed until homogeneous to obtain a mixture as component 6. Then, to the mixture (component 6), cyclopentasiloxane (component 7) was added, stirred and mixed until homogeneous to obtain a copolymer mixture.

2. Components 1 to 5 were mixed until homogeneous to obtain a paste-like mixture.

3. Next, the copolymer mixture and the paste-like mixture were combined and further components 8 to 13 were sequentially added and mixed until homogeneous to obtain an oil phase mixture.

4. Separately, components 14 to 19 were stirred until homogeneous to obtain an aqueous phase mixture.

5. Finally, to the oil phase mixture, the aqueous phase mixture was added with stirring. In this manner, the compositions for external application, i.e., water-in-oil sunscreens of Example 10 and Comparative Example 8 were individually obtained.

TABLE 9

| | | | unit: mass % |
|---|---|---|---|
| | Component | Example 10 | Comparative Example 8 |
| 1 | PEG-9 polydimethylsiloxyethyl dimethicone | 2.00 | 2.00 |
| 2 | Cyclopentasiloxane | 16.00 | 16.00 |
| 3 | Caprylyl methicone | 8.00 | 8.00 |
| 4 | Hydrophobized titanium oxide particles | 4.00 | 4.00 |
| 5 | Hydrophobized zinc oxide particles | 22.00 | 22.00 |
| 6 | Mixture of copolymer of Synthesis Example 2 and ethanol | 4.00 | — |
| 7 | Cyclopentasiloxane | 4.00 | 2.00 |
| 8 | (Dimethicone/vinyl dimethicone) crosspolymer (KSG-15, manufactured by Shin-Etsu Chemical Co., Ltd.) | — | 6.00 |
| 9 | Antioxidant: tocopherol acetate | 0.50 | 0.50 |
| 10 | Ultraviolet absorber: ethylhexyl methoxycinnamate | 7.50 | 7.50 |
| 11 | Isononyl isononanoate | 6.00 | 6.00 |
| 12 | Preservative: caprylyl glycol | 0.50 | 0.50 |
| 13 | Spherical powder: polymethylsilsesquioxane | 4.00 | 4.00 |
| 14 | Purified water | 10.50 | 10.50 |
| 15 | Dipropylene glycol | 4.00 | 4.00 |
| 16 | Magnesium sulfate | 0.50 | 0.50 |
| 17 | Butylene glycol | 2.00 | 2.00 |
| 18 | Ethanol | 4.00 | 4.00 |
| 19 | Preservative: phenoxyethanol | 0.50 | 0.50 |
| | Total | 100.00 | 100.00 |

It was confirmed that the water-in-oil sunscreen of Example 10, in which the copolymer of Synthesis Example 2 was blended, was excellent in cosmetic-effect persistency even if a coating agent is not blended. In contrast, in Comparative Example 8, cosmetic-effect persistency was not sufficient.

[Oil-in-Water Makeup Bases of Example 11 and Comparative Example 9]

Compositions for external application, i.e., oil-in-water makeup bases, was prepared in accordance with the formulations shown in Table 10 as follows.

1. To the copolymer of Synthesis Example 2, the same mass of ethanol was added, stirred and mixed until homogeneous to obtain a mixture as component 1. Then, to the mixture (component 1), components 2 and 3 were added, stirred and mixed until homogeneous to obtain a copolymer mixture.

2. The copolymer mixture and Components 4 to 8 were blended, heated and mixed until homogeneous to obtain an oil phase mixture.

3. Separately, components 9 to 13 were stirred until homogeneous to obtain an aqueous phase mixture. Furthermore, components 16 to 18 were stirred to obtain an ethanol mixture.

4. Finally, to the aqueous phase mixture, the oil phase mixture was added with stirring and further, components 14, 15 and the ethanol mixture were sequentially added and mixed until homogeneous. In this manner, the compositions for external application, i.e., oil-in-water makeup bases, of Example 11 and Comparative Example 9 were individually obtained.

TABLE 10

| | | | unit: mass % |
|---|---|---|---|
| | Component | Example 11 | Comparative Example 9 |
| 1 | Mixture of copolymer of Synthesis Example 2 and ethanol | 3.00 | — |
| 2 | Isononyl isononanoate | 9.00 | 12.00 |
| 3 | Ultraviolet absorber: ethylhexyl methoxycinnamate | 6.50 | 6.50 |
| 4 | PEG-40 STEARATE | 1.00 | 1.00 |
| 5 | Glyceryl stearate | 1.00 | 1.00 |
| 6 | Sorbeth tetraoleate-40 | 0.50 | 0.50 |
| 7 | Behenyl alcohol | 1.00 | 1.00 |
| 8 | Cetearyl alcohol | 1.00 | 1.00 |
| 9 | Pentylene glycol | 3.00 | 3.00 |
| 10 | Butylene glycol | 6.00 | 6.00 |
| 11 | Glycerin | 3.00 | 3.00 |
| 12 | Sodium hyaluronate | 0.05 | 0.05 |
| 13 | Purified water | 53.95 | 53.95 |
| 14 | Mica pearl (mica + titanium oxide) | 5.00 | 5.00 |
| 15 | (Acryloyldimethyltaurate ammonium/VP) copolymer | 0.50 | 0.50 |
| 16 | Preservative: phenoxyethanol | 1.00 | 1.00 |
| 17 | Preservative: caprylyl glycol | 0.50 | 0.50 |
| 18 | Ethanol | 4.00 | 4.00 |
| | Total | 100.00 | 100.00 |

It was confirmed that the oil-in-water makeup base of Example 11, in which the copolymer of Synthesis Example 2 was blended, was excellent in cosmetic-effect persistency even if a coating agent was not blended. In contrast, in Comparative Example 9, cosmetic-effect persistency was not sufficient.

[Face Creams of Example 12 and Comparative Example 10]

Compositions for external application, i.e., face creams, were prepared in accordance with the formulations shown in Table 11 as follows.

1. To the copolymer of Synthesis Example 2, the same mass of ethanol was added, stirred and mixed until homogeneous to obtain the mixture as component 1. Then, to the mixture (component 1), cyclopentasiloxane as component 2 was added, stirred and mixed until homogeneous to obtain a copolymer mixture.

2. Components 3 to 11 were sequentially added to the copolymer mixture and mixed until homogeneous to obtain an oil phase mixture.

3. Separately, components 12 to 18 were stirred until homogeneous to obtain an aqueous phase mixture.

4. Finally, to the oil phase mixtures, the aqueous phase mixture was added with stirring. In this manner, the compositions for external application, i.e., face creams, of Example 12 and Comparative Example 10 were obtained.

TABLE 11

| | Component | Example 12 | Comparative Example 10 |
|---|---|---|---|
| | | unit: mass % | |
| 1 | Mixture of copolymer of Synthesis Example 2 and ethanol | 8.00 | — |
| 2 | Cyclopentasiloxane | 16.00 | 16.00 |
| 3 | Distearyldimonium hectorite | — | 1.50 |
| 4 | Isononyl isononanoate | 4.00 | 4.00 |
| 5 | Cetyl ethyl hexanoate | 8.00 | 8.00 |
| 6 | Meadowfoam oil | 4.00 | 4.00 |
| 7 | Lauryl PEG-9 polydimethylsiloxyethyl dimethicone | 1.00 | 1.00 |
| 8 | (Dimethicone/(PEG-10/15)) cross polymer (KSG-210, manufactured by Shin-Etsu Chemical Co., Ltd.) | 2.00 | 2.00 |
| 9 | (Laurylpolydimethylsiloxyethyldimethicone/bis-vinyl dimethicone) crosspolymer (KSG-16, manufactured by Shin-Etsu Chemical Co., Ltd.) | — | 4.00 |
| 10 | Preservative: caprylyl glycol | 0.50 | 0.50 |
| 11 | Spherical powder: polymethylsilsesquioxane | 5.00 | 5.00 |
| 12 | Purified water | 42.30 | 42.80 |
| 13 | Glycerin | 3.00 | 3.00 |
| 14 | Butylene glycol | 3.00 | 3.00 |
| 15 | Sodium citrate | 0.20 | 0.20 |
| 16 | Sodium chloride | 0.50 | 0.50 |
| 17 | Ethanol | 2.00 | 4.00 |
| 18 | Preservative: phenoxyethanol | 0.50 | 0.50 |
| | Total | 100.00 | 100.00 |

It was confirmed that the face cream of Example 12, in which the copolymer of Synthesis Example 2 was blended in a large amount, was stable even if a thickener was not blended. A face cream having characteristic viscosity was obtained. In contrast, in Comparative Example 10, since a thickener was added for stabilization, the user felt sticky when used.

[Hand Creams of Example 13 and Comparative Example 11]

Compositions for external application, i.e., hand cream, were prepared in accordance with the formulations shown in Table 12, as follows.

1. To the copolymer of Synthesis Example 2, the same mass of ethanol was added, stirred and mixed until homogeneous to obtain a mixture as component 1. Then, to the mixture (component 1), cyclopentasiloxane as component 2 was added, stirred and mixed until homogeneous to obtain a copolymer mixture.

2. Components 3 to 12 were sequentially added to the copolymer mixture and mixed until homogeneous to obtain an oil phase mixture.

3. Separately, components 13 to 18 were stirred until homogeneous to obtain an aqueous phase mixture.

4. Finally, to the oil phase mixture, the aqueous phase mixture was added with stirring. In this manner, the compositions for external application, i.e., hand creams, of Example 13 and Comparative Example 11 were obtained.

TABLE 12

| | Component | Example 13 | Comparative Example 11 |
|---|---|---|---|
| | | unit: mass % | |
| 1 | Mixture of copolymer of Synthesis Example 2 and ethanol | 8.00 | — |
| 2 | Cyclopentasiloxane | 18.00 | 18.00 |
| 3 | Quaternium-18 bentonite | 1.00 | 2.00 |
| 4 | Isononyl isononanoate | 4.00 | 4.00 |
| 5 | Ultraviolet absorber: ethylhexyl methoxycinnamate | 6.00 | 6.00 |
| 6 | Dimethicone 6cs | 4.00 | 4.00 |
| 7 | Coating agent: trimethylsiloxysilicate (KF7312T, manufactured by Shin-Etsu Chemical Co., Ltd.) | — | 1.00 |
| 8 | Lauryl PEG-9 polydimethylsiloxyethyl dimethicone | 1.00 | 2.00 |
| 9 | (Dimethicone/(PEG-10/15)) cross polymer (KSG-210, manufactured by Shin-Etsu Chemical Co., Ltd.) | 2.00 | 2.00 |
| 10 | (Lauryl polydimethylsiloxyethyl dimethicone/bis-vinyl dimethicone) crosspolymer (KSG-16, manufactured by Shin-Etsu Chemical Co., Ltd.) | — | 5.00 |
| 11 | Preservative: caprylyl glycol | 0.50 | 0.50 |
| 12 | Spherical powder: polymethylsilsesquioxane | 5.00 | 5.00 |
| 13 | Purified water | 39.30 | 39.30 |
| 14 | Glycerin | 6.00 | 6.00 |
| 15 | Butylene glycol | 2.00 | 2.00 |
| 16 | Sodium citrate | 0.20 | 0.20 |
| 17 | Ethanol | 2.00 | 2.00 |
| 18 | Preservative: phenoxyethanol | 1.00 | 1.00 |
| | Total | 100.00 | 100.00 |

The hand cream of Example 13, in which the copolymer of Synthesis Example 2 was blended in a large amount, was stable even if a thickener was not blended and a hand cream having characteristic viscosity was obtained. Furthermore, it was confirmed that the hand cream of Example 13, in which the copolymer of Synthesis Example 2 was blended, was excellent in cosmetic-effect persistency and water resistant even if a coating agent was not blended. In contrast, in Comparative Example 11, since a thickener was added for stabilization, the user felt sticky when used.

INDUSTRIAL APPLICABILITY

The composition for external application of the present invention can be suitably used as a skin cosmetic (including medicated cosmetic) such as a liquid foundation, a cream foundation, a sunscreen, a makeup base, a face cream, a hand cream and a mascara; and a hair cosmetic such as a shampoo, a hair rinse, a hair treatment and a hair cream; and an ointment.

The invention claimed is:

1. A composition for external application to skin and/or hair comprising an acrylic silicone graft copolymer, which contains 2 to 25 mass % of a constitutional unit represented by formula (I), 55 to 85 mass % of a constitutional unit represented by formula (II) and 2 to 20 mass % of a constitutional unit represented by formula (III):

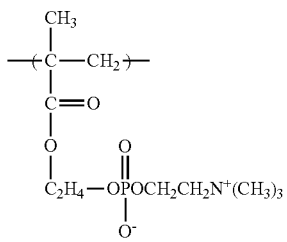

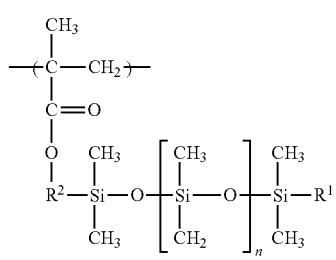

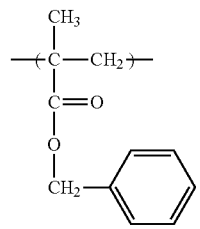

wherein $R^1$ is an alkyl group having 1 to 4 carbon atoms; $R^2$ is an alkylene group having 2 to 10 carbon atoms; and n is an integer of 1 to 100 and further comprising an oily component present in a liquid state at room temperature of 25° C.

2. The composition according to claim 1, wherein the oily component present in a liquid state at room temperature of 25° C. is is at least one selected from the group consisting of a natural oil, a hydrocarbon oil, an ester oil and a silicone oil.

3. The composition according to claim 1, wherein the acrylic silicone graft copolymer is contained in an amount of 0.1 to 20 mass % based on the total mass of the composition.

4. A method for producing the composition according to claim 1, comprising blending a mixture of an acrylic silicone graft copolymer and an oily component present in a liquid state at room temperature of 25° C.

5. A cosmetic method for skin care or makeup, comprising applying the composition according to claim 1 to skin.

6. The composition according to claim 2, wherein the acrylic silicone graft copolymer is contained in an amount of 0.1 to 20 mass % based on the total mass of the composition.

7. A method for producing the composition according to claim 2, comprising blending a mixture of an acrylic silicone graft copolymer and an oily component present in a liquid state at room temperature of 25° C.

8. A method for producing the composition according to claim 3, comprising blending a mixture of an acrylic silicone graft copolymer and an oily component present in a liquid state at room temperature of 25° C.

9. A makeup product comprising the composition according to claim 1.

10. A cosmetic method for skin care or makeup, comprising applying the composition according to claim 2 to skin.

11. A cosmetic method for skin care or makeup, comprising applying the composition according to claim 3 to skin.

12. A method for producing the composition according to claim 6, comprising blending a mixture of an acrylic silicone graft copolymer and an oily component present in a liquid state at room temperature of 25° C.

* * * * *